United States Patent [19]

Rieger

[11] Patent Number: 5,824,089
[45] Date of Patent: Oct. 20, 1998

[54] CERAMIC BODIES OF ZIRCONIUM OXIDE STABILIZED WITH YTTRIUM OXIDE

[75] Inventor: Wolfhart Rieger, Zur Mühle, Switzerland

[73] Assignee: Metoxit AG, Thayngen, Switzerland

[21] Appl. No.: 879,081

[22] Filed: Jun. 19, 1997

Related U.S. Application Data

[63] Continuation of Ser. No. 613,326, Mar. 11, 1996, abandoned, which is a continuation of Ser. No. 237,621, May 4, 1994, abandoned.

[30] Foreign Application Priority Data

May 7, 1993 [CH] Switzerland .......................... 01410/93

[51] Int. Cl.[6] ........................................................ A61F 2/28
[52] U.S. Cl. ........................... 623/16; 628/11; 433/201.1; 501/103
[58] Field of Search .................... 623/11, 16; 433/201.1, 433/206; 501/94, 103

[56] References Cited

U.S. PATENT DOCUMENTS

| | | | |
|---|---|---|---|
| 4,595,663 | 6/1986 | Krohn et al. | 623/66 |
| 4,748,138 | 5/1988 | Watanabe et al. | 501/103 |
| 4,753,902 | 6/1988 | Ketcham | 501/103 |
| 4,983,182 | 1/1991 | Kijima et al. | 433/201.1 |
| 5,122,317 | 6/1992 | Chen et al. | 264/60 |
| 5,358,645 | 10/1994 | Hong et al. | 210/761 |
| 5,556,816 | 9/1996 | Kim et al. | 501/103 |

*Primary Examiner*—Paul B. Prebilic
*Attorney, Agent, or Firm*—Bachman & LaPointe, P.C.

[57] ABSTRACT

An yttrium-stabilized zirconium oxide in predominantly tetragonal form is of the composition $ZrO_2$ 92.1%–93.5%, $Y_2O_3$ 4.5%–5.5%, $HfO_2$ 1.8%–2.2%, and impurities at most 0.2%, for the production of a sintered semi-finished article as a starting material for manufacture of a prosthesis.

6 Claims, No Drawings

CERAMIC BODIES OF ZIRCONIUM OXIDE STABILIZED WITH YTTRIUM OXIDE

This is a continuation of application Ser. No. 08/613,326 filed on Mar. 11, 1996, which is a continuation of application Ser. No. 08/237,621 filed on May 4, 1994 now abandoned.

BACKGROUND OF THE INVENTION

The invention concerns a material for prostheses and more particularly a ceramic material for the production of prostheses.

Metallic and ceramic materials can be used for the production of prostheses, whether they are endoprostheses or exoprostheses. Chromium-cobalt steels and titanium alloys have gained entry into the prosthesis art as metallic materials. Both those materials are essentially biocompatible, being therefore compatible with the body so as to minimize rejection problems. Chromium-cobalt steels are used as a material for endoprostheses as such steels have proven themselves to be resistant to body fluids with a hydrogen ion concentration of constantly near 7 (pH 7=neutral). On the other hand that resistance is not enjoyed in the mouth region with considerable fluctuations in pH-value. In contrast to chromium-cobalt steels titanium alloys (TiAl6N, TiAl6Nb) are resistant to fluctuations in pH-value. They are therefore used as materials for endoprostheses and for prostheses in the mouth region (exoprostheses), but a disadvantage thereof, in comparison with chromium-cobalt steels, is that those titanium alloys involve a degree of strength which is not entirely adequate. However both these metal materials can be comparatively easily mechanically worked, that is to say machined and cut.

As an alternative to such metal materials, ceramic materials have also shown themselves to be suitable for endoprostheses and exoprostheses. A number of requirements have to be made in respect of ceramic materials, for example as follows. They must be bioinert, that is to say, resistant to body fluids. To avoid the absorption of body fluids, ceramic prostheses and in particular endoprostheses should not be porous. They must also exhibit resistance to corrosion, that is to say, surface attack on or erosion of the prostheses is to be prevented. Further requirements involved are a degree of strength which is appropriate for the purpose of use of the prosthesis and biocompatibility. Ceramic materials have to comply with all the foregoing requirements, and the failure to fulfil one requirement means that a ceramic material can no longer be considered for prosthetic purposes.

Two ceramic materials have proven themselves suitable for load-bearing endoprostheses and exoprostheses, namely aluminium oxide (Al2O3) with an Al2O3 proportion of 99.85%, with the balance being other constituents, and zirconium oxide (ZrO2) of predominantly tetragonal structure, stabilized by magnesium oxide (MgO2) or by an oxide of the rare earths, preferably yttrium oxide (Y2O3) or cerium oxide (CeO2).

Clear limits are set on the use of the above-indicated ceramic materials in relation to prostheses, insofar as they appear to be less suited to the production of prostheses of complicated three-dimensional configurations, for example tooth, finger or spine part prostheses and so forth. Presintered Al2O3 semi-finished prosthesis articles which have to be subjected to dense sintering after finishing machining are distinguished by a high level of hardness and major difficulty in terms of machineability, which meant that Al2O3 was not used in the dental area, for example insofar as prostheses such as crowns and bridges may be of wall thicknesses down to a minimum of 0.2 mm. The situation is comparable with ZrO2. In sintered form it is even more difficult to machine in comparison with Al2O3. In porous form it is comparatively easy to machine and would therefore be suitable in that condition for shaping by machine of complicated three-dimensional structures, that is to say bodies, if dense sintering were not generally required in connection with prostheses, to avoid porosity. In the dental area, besides dense or consolidating sintering for eliminating porosity, such sintering is additionally indispensable for the production of prostheses involving filigree wall portions and/or thin web portions.

It is the dense or consolidating sintering of prefabricated prosthesis parts, necessitating finishing machining and cleaning, that has also imposed limits on ZrO2 in terms of its utility for the production of prostheses, insofar as it is possible to use that ceramic material for the production of relatively large load-bearing prostheses, but not small, structurally complicated prostheses such as tooth or finger prostheses. Therefore zirconium oxide (ZrO2) of the above-described kind involves a limited range of uses.

SUMMARY OF THE INVENTION

An object of the present invention is so to enhance the range of uses of ZrO2 that it can be used in a more versatile fashion for prosthesis manufacture.

Another object of the present invention is to provide a zirconium oxide which is capable of covering a range of prosthesis products from large load-bearing prostheses to small-size and large-size implants of complicated configurations, with the minimum of ZrO2 material variants.

A still further object of the present invention is to provide a prosthesis material which contributes substantially to simplifying manufacture of a prosthesis therefrom.

In accordance with the principles of the present invention the foregoing and other objects are attained by an yttrium oxide-stabilized zirconium oxide in predominantly tetragonal form, of the composition ZrO2 92.1%–93.5%, Y2O3 4.5%–5.5%, HfO2 1.8%–2.2%, and impurities at most 0.2%, for the production of a densely sintered semi-finished article, for example plates, disks, cups or the like, as a starting material for a prosthesis.

The material according to the present invention is ceramic, bioinert and resistant to corrosion, and in comparison with the above-mentioned metallic materials it has a markedly higher degree of strength and it is demonstrably biocompatible. Those advantages are further supplemented by the consideration that, for the production of prostheses, the material according to the invention can firstly be processed to provide a densely sintered semi-finished article, from which then a prosthesis can be produced by machining.

Although the sintering operation cannot be entirely avoided in regard to use of the material according to the invention, it is however, in contrast to the present practice, moved in the course of manufacture of a prosthesis, towards the stage of a semi-finished article, in regard to which the problems of contraction and shrinkage, finishing machining, and cleaning of impurities are generally of no importance.

EXAMPLE

An amount of between 92.1% and 93.5% of ZrO2 is mixed with between 4.5% and 5.5% of Y2O3 and between 1.8% and 2.2% of HfO2, with all impurities (SiO2, Al2O3, TlO2) constituting at most 0.2% (all percentages are percent by weight), shaped to afford a semi-manufactured article, for example a plate, disk or cup or the like, and that article is then densely sintered. The semi-finished article is distinguished by a high level of strength, medium toughness or ductility, and small grain size. The article can be subjected to a machining operation to put it into the form of an endoprosthesis or exoprosthesis of any suitable dimension such as large or very small dimensions, possibly of complicated structure and possibly with a filigree wall configuration.

It will be appreciated that the above-described material according to the invention and the Example of manufacture thereof have been set forth solely by way of illustration of the principles of the present invention and that various modifications and alterations may be made without thereby departing from the spirit and scope of the invention.

What is claimed is:

1. A prosthetic article comprising a ceramic body comprising a yttrium oxide stabilized zirconium oxide of predominantly tetragonal form having a composition consisting essentially of between 92.1 to 93.5% $ZrO_2$, between 4.5 to 5.5% $Y_2O_3$, between 1.8 to 2.2% $HfO_2$, and impurities not to exceed 0.2% of the total.

2. A prosthetic article comprising a ceramic body consisting essentially of $ZrO_2$, $HfO_2$, $Y_2O_3$ and impurities wherein the $Y_2O_3$ is present in an amount of between 4.5 to 5.5 wt %, the balance being essentially $ZrO_2$ and $HfO_2$ with impurities not to exceed 0.2 wt % of the total.

3. A prosthetic article according to claim 9 wherein said $ZrO_2$ is present in an amount of greater than or equal to 92.1 wt %.

4. A prosthetic article according to claim 10 wherein said $HfO_2$ is present in an amount of greater than or equal to 1.8 wt %.

5. A prosthetic article according to claim 9 wherein said ceramic body is predominantly tetragonal in structure.

6. A prosthetic article according to claim 12 wherein said ceramic body is bioinert and resistant to corrosion.

* * * * *

UNITED STATES PATENT AND TRADEMARK OFFICE
CERTIFICATE OF CORRECTION

PATENT NO.   :  5,824,089
DATED        :  OCTOBER 20, 1998
INVENTOR(S)  :  WOLFHART RIEGER

It is certified that error appears in the above-identified patent and that said Letters Patent is hereby corrected as shown below:

On the title page, item [54] and column 1, line 1;

IN THE TITLE, DELETE "CERAMIC BODIES" AND INSERT --PROSTHETIC ARTICLES-- IN ITS PLACE.

IN THE ABSTRACT, LINE 4, DELETE ", FOR" AND INSERT --. THIS OXIDE COMPOSITION IS USED IN---.

COLUMN 4, CLAIM 3, LINE 1, DELETE "CLAIM 9" AND INSERT --CLAIM 2-- IN ITS PLACE.

COLUMN 4, CLAIM 4, LINE 1, DELETE "CLAIM 10" AND INSERT --CLAIM 3-- IN ITS PLACE.

COLUMN 4, CLAIM 5, LINE 1, DELETE "CLAIM 9" AND INSERT --CLAIM 2-- IN ITS PLACE.

COLUMN 4, CLAIM 6, LINE 1, DELETE "CLAIM 12" AND INSERT --CLAIM 5-- IN ITS PLACE.

Signed and Sealed this

Twenty-third Day of November, 1999

Attest:

Q. TODD DICKINSON

*Attesting Officer*        Acting Commissioner of Patents and Trademarks